(12) United States Patent
Williams et al.

(10) Patent No.: US 6,391,578 B2
(45) Date of Patent: May 21, 2002

(54) METHOD AND DEVICES FOR PARTITIONING BIOLOGICAL SAMPLE LIQUIDS INTO MICROVOLUMES

(75) Inventors: Michael G. Williams, Vadnais Heights; Kurt J. Halverson, Lake Elmo; Gary E. Krejcarek, White Bear Lake; Ai-Ping Wei, Woodbury; James G. Berg, Lino Lakes; Peter D. Wickert, St. Paul; Clyde D. Calhoun; Mark K. Debe, both of Stillwater, all of MN (US); Jean Qiu, Andover, MA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/824,160

(22) Filed: Apr. 2, 2001

Related U.S. Application Data

(63) Continuation of application No. 08/997,337, filed on Dec. 23, 1997, which is a continuation-in-part of application No. 08/838,397, filed on Apr. 9, 1997, now abandoned.

(51) Int. Cl.$^7$ .................................................. C12Q 1/06
(52) U.S. Cl. ............................. 435/39; 435/29; 435/31; 435/34; 435/288.3; 435/288.4
(58) Field of Search ............................. 435/29, 31, 34, 435/39, 288.4, 288.3

(56) References Cited

U.S. PATENT DOCUMENTS

| | | |
|---|---|---|
| 3,010,880 A | 11/1961 | Littman et al. |
| 3,509,026 A | 4/1970 | Sanders |
| 3,856,628 A | 12/1974 | Sbarra |
| 3,881,993 A | 5/1975 | Freake et al. |
| 3,929,583 A | 12/1975 | Sharpe et al. |
| 4,018,652 A | 4/1977 | Lanham et al. |
| 4,264,560 A | 4/1981 | Natelson |
| 4,335,206 A | 6/1982 | Wilkins et al. |
| 4,485,171 A | 11/1984 | Ikeda et al. |
| 4,682,891 A | 7/1987 | De Macraio et al. |
| 4,777,021 A | 10/1988 | Wertz et al. |
| 4,803,154 A | 2/1989 | Uo et al. |
| 4,806,316 A | 2/1989 | Johnson et al. |
| 4,906,439 A | 3/1990 | Grenner |
| 5,219,462 A | 6/1993 | Bruxvoort et al. |
| 5,229,163 A | 7/1993 | Fox |
| 5,236,827 A | 8/1993 | Sussman et al. |
| 5,338,666 A | 8/1994 | Monthony |
| 5,409,838 A | 4/1995 | Wickert |
| 5,457,030 A | 10/1995 | Badal et al. |
| 5,494,823 A | 2/1996 | Kashihara et al. |
| 5,498,525 A | 3/1996 | Rees et al. |
| 5,503,803 A | 4/1996 | Brown |
| 5,700,655 A | 12/1997 | Croteau et al. |
| 5,707,799 A | 1/1998 | Hansmann et al. |

FOREIGN PATENT DOCUMENTS

| | | |
|---|---|---|
| DE | 32 26 407 C2 | 5/1985 |
| DE | 36 31 066 A1 | 4/1988 |
| DE | 37 32 142 A1 | 4/1989 |
| DE | 42 18 917 A1 | 12/1993 |
| EP | 0 321 736 B1 | 6/1989 |
| EP | 0 459 093 A2 | 12/1991 |
| EP | 0 496 200 A2 | 7/1992 |
| EP | 0 656 420 A1 | 6/1995 |
| EP | 0 751 393 A2 | 1/1997 |
| EP | 0 795 600 A1 | 9/1997 |
| EP | 0 834 729 A2 | 4/1998 |
| EP | 0 928 830 A1 | 7/1999 |
| GB | 1 437 404 | 5/1976 |
| JP | 63096558 | 4/1988 |
| JP | 04051890 A | 2/1992 |
| JP | 04051900 A | 2/1992 |
| JP | 04265860 | 9/1992 |
| JP | 06062893 A | 3/1994 |
| JP | 08000286 A | 1/1996 |
| JP | 08140664 A | 6/1996 |
| JP | 09019282 A | 1/1997 |
| WO | WO 92/12257 | 7/1992 |
| WO | WO 93/11727 | 6/1993 |
| WO | WO 93/19199 | 9/1993 |
| WO | WO 94/11489 | 5/1994 |
| WO | WO 95/23026 | 8/1995 |
| WO | WO 96/14432 | 5/1996 |
| WO | WO 96/15435 | 5/1996 |
| WO | WO 96/40980 | 12/1996 |
| WO | WO 97/05274 | 2/1997 |
| WO | WO 97/08291 | 3/1997 |
| WO | WO 97/12242 | 4/1997 |
| WO | WO 97/13839 | 4/1997 |
| WO | WO 97/18455 | 5/1997 |
| WO | WO 97/24432 | 7/1997 |
| WO | WO 97/37036 | 10/1997 |
| WO | WO 97/49987 | 12/1997 |
| WO | WO 98/31466 | 7/1998 |
| WO | WO 98/45406 | 10/1998 |
| WO | WO 99/06589 | 2/1999 |
| WO | WO 99/32601 | 7/1999 |

OTHER PUBLICATIONS

Product Brochure: SimPlate™ Total Count Plate from Idexx Laboratories, Inc., updated.

*Primary Examiner*—Leon B. Lankford, Jr.
(74) *Attorney, Agent, or Firm*—James A. Rogers; Christopher D. Gram; Robert W. Sprague

(57) ABSTRACT

A method for partitioning an aqueous biological liquid sample into discrete microvolumes for detection and enumeration of microorganisms is described. The method involves distributing microvolumes of a sample to a plurality of hydrophilic liquid-retaining zones of a culture device, where each liquid-retaining zone is surrounded by a portion of a hydrophobic "land" area. Also disclosed are devices for carrying out these methods.

54 Claims, 5 Drawing Sheets

METHOD AND DEVICES FOR PARTITIONING BIOLOGICAL SAMPLE LIQUIDS INTO MICROVOLUMES

This application is a continuation of prior application, U.S. Ser. No. 08/997,337, filed Dec. 23, 1997, which is a continuation-in-part of U.S. Ser. No. 08/838,397, filed Apr. 9, 1997, abandoned.

FIELD

This invention relates to methods and devices for partitioning biological samples into microvolume aliquots, based on the tendency for aqueous liquids to be retained within hydrophilic zones of the devices while being substantially excluded from hydrophobic areas of the devices, and detecting and enumerating microorganisms present within the samples.

BACKGROUND

The detection and enumeration of microorganisms is practiced in numerous settings, including the food-processing industry (testing for the contamination of food by microorganisms such as $E.\ coli$ and $S.\ aureus$), the health care industry (testing of patient samples and other clinical samples for infection or contamination), environmental testing industry, the pharmaceutical industry, and the cosmetic industry.

Growth-based detection and enumeration of microorganisms is commonly practiced using either liquid nutrient media (most probable number analysis (MPN)) or semi-solid nutrient media (agar petri dishes). Enumeration using the liquid MPN method is typically achieved by placing serial 10-fold dilutions of a sample of interest in replicate sets of tubes containing selective media and chemical indicators. The tubes are incubated at elevated temperature (24–48 hours) followed by examination for growth of organisms. A statistical formula, based on the volume of sample tested and the number of positive and negative tubes for each set, is used to estimate the number of organisms present in the initial sample.

This method of performing MPN analysis has several disadvantages. It is labor intensive because of the multiple diluting and pipetting steps necessary to perform the analysis. In addition, in practice it is only practical to use replicate sets of about three to five tubes for each dilution. As a result, the 95% confidence limits for an MPN estimate for microbial concentration are extremely wide. For example, a three tube MPN estimate of 20 has 95% confidence limits ranging from 7 to 89. Furthermore, results typically are not obtainable in less than twenty-four hours.

In contrast to the method described above, a direct count of viable microorganisms in a sample can be achieved by spreading the sample over a defined area using nutrient media containing a gelling agent. The gelling agent (agar) prevents diffusion of the organisms during incubation (24–48 hours), producing a colony in the area where the original organism was deposited. There is, however, a limit to the number of colonies that can fit on a given area of nutrient media before fusion with neighboring colonies makes counting difficult. This usually necessitates performing several dilutions for each sample. In addition, the classes of chemical indicator molecules that can be used for identifying individual types of microorganisms present within a mixed population are limited to those that produce a product that is insoluble in the gelled media. Furthermore, rapid detection, i.e., in less than twenty-four hours, and enumeration is not feasible using this method.

In addition to these disadvantages, both the currently used MPN analysis and gel-based systems require a relatively long incubation time before a positive result can be detected.

SUMMARY

The invention is based on the discovery that biological liquid samples can be partitioned into discrete microvolumes with only minimal manipulation on the part of an operator. The method of partitioning employs devices that have hydrophilic liquid-retaining zones surrounded by hydrophobic "land" areas. The methods and devices provide a system for the detection and enumeration of microorganisms and other biological materials that solves the problems associated with currently used systems. The system is a liquid-based system, allowing efficient and effective partitioning of the sample into discrete microvolumes for testing, and allows for rapid detection and enumeration.

In the case of MPN analysis for the detection and enumeration of microorganisms, the approaches described herein allow for the use of water-soluble indicator species, and reduce or eliminate the need for the several dilutions typically required in current MPN analysis.

In general, the invention features a method for partitioning an aqueous liquid sample, into discrete microvolumes, comprising a) providing a device for culturing a microorganism, said device having an assay surface, the assay surface comprising hydrophilic liquid-retaining zones and a hydrophobic land area between the zones, each zone having a microvolume capacity of liquid retention; and b) contacting the liquid sample with the assay surface such that the liquid sample is partitioned into the hydrophilic liquid-retaining zones.

The zones may comprise a coating or deposition of assay reagent, such as a nutrient medium or indicator substance. Appropriate indicator substances include without limitation chromogenic indicators, fluorescent indicators, luminescent indicators and electrochemical indicators.

The zones may be of uniform size, with each zone having a liquid retention capacity of about 0.01 to about 25 microliters, more preferably about 1 to about 2 microliters.

The culture device can have, for example, about 10 to about 10,000 hydrophilic liquid-retaining zones, more preferably about 400 to about 600 hydrophilic liquid-retaining zones.

The hydrophilic liquid-retaining zones may comprise microvolume wells surrounded by a hydrophobic land area. Alternatively, the culture device may have a land area comprising a treated nanostructured film. In further alternative embodiments, the hydrophilic liquid-retaining zones may comprise hydrophilic fiber material projecting from the assay surface. The fiber material can be constructed of hydrophilic absorbent discs or of hydrophilic nonwoven fiber loop material. Hydrophilic absorbent discs may have media provided thereon to facilitate growth of microorganisms. The media may be selective for one or more types of microorganisms. The discs are biocompatible with the microorganisms such that the materials do not substantially interfere with the growth or detection of the microorganisms.

In an alternative embodiment, the culture device may comprise a plurality of sets of hydrophilic liquid-retaining zones, each of the sets having zones of uniform size, the sets varying in liquid retention capacity, and the device having at least two sets of zones.

In another aspect, the invention features a culture device for detection or enumeration of microorganisms, the device comprising an assay surface, the assay surface comprising hydrophilic liquid-retaining zones and a hydrophobic land area between the zones, each zone having a microvolume capacity of liquid retention, and at least some of the zones comprising an assay reagent.

As used herein, the term "microorganism" includes all microscopic living organisms and cells, including without limitation bacteria, mycoplasmas, rickettsias, spirochetes, yeasts, molds, protozoans, as well as microscopic forms of eukaryotic cells, for example single cells (cultured or derived directly from a tissue or organ) or small clumps of cells. Microorganisms are detected and/or enumerated not only when whole cells are detected directly, but also when such cells are detected indirectly, such as through detection or quantitation of cell fragments, cell-derived biological molecules, or cell by-products.

As used herein, "microvolume" refers to a volume of less than about 25 microliters, and includes volumes in the sub-microliter range.

The terms "hydrophobic" and "hydrophilic" are herein given the meanings commonly understood in the art. Thus, a "hydrophobic" material has relatively little or no affinity for water or aqueous media, while a "hydrophilic" material has relatively strong affinity for water or aqueous media. The relative hydrophobicities and hydrophilicities of the devices described herein are such as to ensure partitioning of liquid samples substantially into the described hydrophilic liquid-retaining zones upon application of the sample. The required levels of hydrophobicity and hydrophilicity may vary depending on the nature of the sample, but may be readily adjusted based on simple empirical observations of the liquid sample when applied to the devices.

The term "electrochemical" means a chemical indicator that changes the resistance of conductance of the sample upon reaction with the microorganism.

Other advantages of the invention will be apparent from the following detailed description and the figures.

BRIEF DESCRIPTION OF THE FIGURES

FIG. 7b is an expanded top view of the device depicted in FIG. 7a.

DETAILED DESCRIPTION

Figure 1:
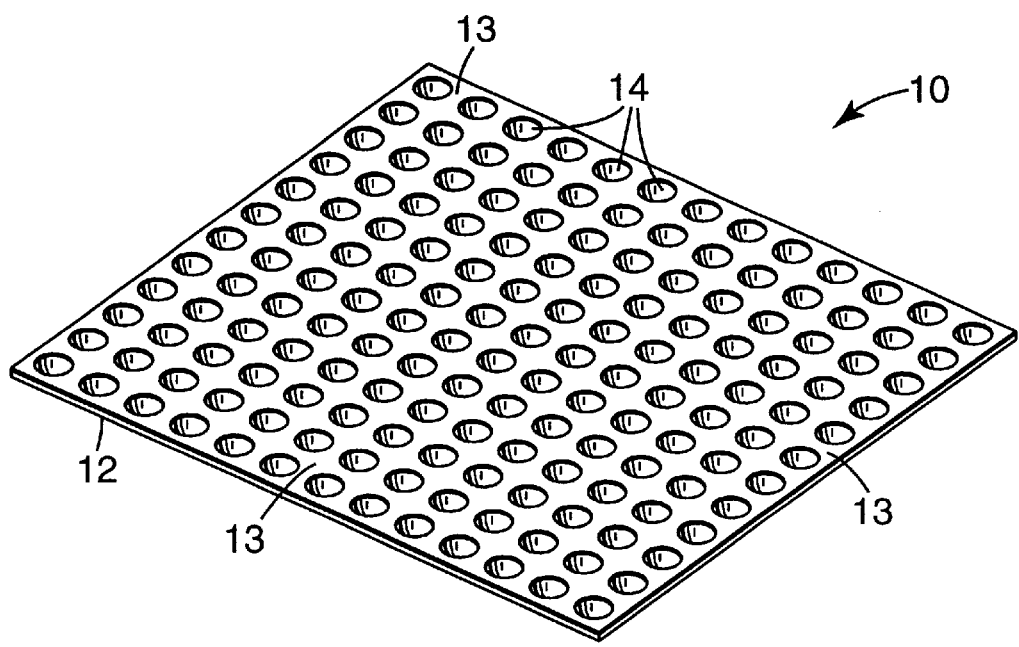
FIG. 1 is a perspective view of one embodiment of an assay device.

This invention relates to methods and devices for partitioning of biological samples into microvolume liquid sample aliquots for signal-based detection and enumeration of microorganisms in liquid samples.

Among the problems encountered in the art relating to the testing of liquid samples for microorganisms are relatively lengthy incubation times, the need to undertake multiple pipetting operations for aliquots being tested, and the need for a relatively large volume of sample for testing.

The present invention provides a solution to these and other problems associated with such testing. Methods and devices are provided for partitioning a liquid sample into microvolume compartments of a test device, with only minimal manipulation of the liquid sample required of the laboratory technician or other operator. In one embodiment, the invention provides absorbent disc materials that are absorbent yet are biocompatible. These materials are also compatible with fluorescent indicator systems. The materials lend themselves easily to the manufacturing process.

The present inventors have discovered that the use of microvolumes in signal-based detection of microorganisms in liquid samples results in remarkably shorter incubation times required to produce a detectable signal. Because shorter incubation times are highly desirable in this field, this feature of the invention provides a distinct advantage.

In addition to achieving shorter incubation times, the use of microvolumes in the testing of liquid samples may allow for the use of substantially smaller test samples. Very small volume test samples are sometimes necessary due to very small volume sample sources. Small volume liquid test samples are also sometimes desirable, for example to ease handling or transport of the sample to a testing facility.

The present inventors have developed a number of novel devices for partitioning of biological liquid samples into discrete microvolumes within hydrophilic liquid-retaining zones (also referred to herein as "liquid-retaining zones" or "zones"). Non-limiting examples of these devices include: micro-embossed or pressed films having a plurality of microcompartments, for example microvolume wells, functioning as liquid-retaining zones, with the area between the wells ("land area") being hydrophobic and the wells being hydrophilic; nanostructured hydrophobic films in which discrete liquid-retaining zones of the film are hydrophilic and are adapted to retain microvolumes of a liquid sample for testing; and devices having hydrophilic liquid-retaining zones and hydrophobic land areas, where a given hydrophilic zone is fabricated from hydrophilic fiber material and projects upward or downward from the plane of the surrounding land area. One particularly useful example of a device of the present invention is a device having hydrophilic liquid-retaining zones and hydrophobic land areas, where a given hydrophilic zone is fabricated from hydrophilic fiber material in the form of a disc that projects upward from the plane of the surrounding land area.

Advantageously, the above-summarized devices allow for the testing of liquid samples using microvolume aliquots in a single device, eliminating the need for separate vessels in such testing. A test sample may be distributed among hundreds or even thousands of discrete liquid-retaining zones, i.e., hydrophilic wells or discs, substantially increasing the number of data points in a test of the liquid sample.

A particularly useful application of these methods and devices is in the growth-based detection and enumeration of microorganisms in liquid test samples. Such growth-based detection and enumeration is very important in the testing of food, environmental, clinical, pharmaceutical, cosmetic, and other samples for contamination by microorganisms. The methods and devices of this invention allow for the efficient, accurate, convenient, and cost-effective testing of such samples. A preferred use of the methods and devices of this invention in such microbiological testing is in MPN. In traditional MPN, a sample of interest is serially diluted (10 fold) and pipetted in equal amounts into replicate sets of tubes containing selective growth media and chemical indicators. The tubes are incubated at elevated temperature for about 24–48 hours followed by examination for growth of organisms. A statistical formula, based on the number of positive and negative tubes for each set, is used to estimate the number of organisms present (per volume) in the initial sample As currently used, this traditional method has several disadvantages. It is labor intensive because of the multiple diluting and pipetting steps required to perform the analysis. As a practical matter, only replicate sets of about three to five tubes for each dilution are commonly used. As a result, the 95% confidence limits for an MPN estimate of microbial concentration using this method are extremely wide. For example, a nine tube (3 ten-fold dilutions) MPN estimate of 20 has 95% confidence limits ranging from 7 to 89.

The use of the methods and devices of the present invention in MPN analysis overcomes several of the above-noted disadvantages. The amount of labor is greatly reduced because no pipetting into individual tubes is necessary, and very little or no agitation or other manipulations are required. Instead, the liquid sample is distributed to microvolume liquid-retaining zones by simply contacting the liquid sample with the device. In addition, fewer sample dilutions are necessary when large numbers of liquid-retaining zones are present in the device. The relatively large number of liquid-retaining zones also provides a more accurate estimate of microbial concentration. This is because the correspondingly larger number of data points provides a correspondingly narrower confidence limit interval.

Accordingly, the present invention provides a method for detecting and enumerating a microorganism in a liquid test sample. The method involves distributing microvolumes of the test sample to a plurality of hydrophilic liquid-retaining zones of an assay device. The assay device may be any device that includes an assay surface having a plurality of hydrophilic liquid-retaining zones, where each zone has a microvolume capacity of liquid retention. The device also includes a land area between the zones that is hydrophobic and remains substantially free of liquid after the biological sample has become distributed into the liquid-retaining zones. Non-limiting examples of such assay devices include those described herein.

The liquid-retaining zones in the assay device preferably are of uniform size and each zone has a liquid-retention capacity of about 0.01 to about 25 microliters of the liquid sample. Preferably, each zone has a liquid retention capacity of about 0.1 to about 10 microliters, and more preferably about 1 to about 2 microliters. The assay device preferably contains between 1 and about 100,000 liquid-retaining zones, more preferably about 10 to about 10,000 zones, even more preferably about 200 to about 5,000 zones and most preferably about 400 to about 600 zones.

The use of a device having about 400 to about 600 hydrophilic liquid-retaining zones is particularly useful in the context of testing a liquid sample for microorganism concentration using MPN. Certain regulatory requirements may dictate that a testing method must be able to detect one microorganism in a one-to-five-milliliter sample. Such a sample size is standard in the food processing industry for microbiological testing. Thus, for example, an assay device having 500 hydrophilic liquid-retaining zones, where each zone has a liquid capacity of about 2 microliters, would be very useful for testing a 1-ml sample. A liquid-retention zone having a capacity of 2 microliters allows for rapid development of a detectable signal in accordance with the invention, and the use of about 400 to about 600 zones provides a sufficiently large number of data points to substantially improve the confidence interval for an MPN calculation. In addition, it is feasible to perform a manual count of liquid-retaining zones testing positive for the microorganism. Use of devices having substantially more than 400 liquid-retaining zones may require, as a practical matter, instrument-assisted or automated counting.

The liquid test sample may be any sample of interest, from any source. The sample may be distributed to the plurality of liquid-retaining zones directly, or the sample may be diluted before distribution to the zones. The determination as to whether sample dilution is necessary will depend on a variety of factors such as sample source and age, and such determination is a routine matter to those of skill in the art.

The liquid test sample may include selective nutrient growth media for the microorganism of interest, and/or an indicator substance that produces a signal in the presence of the growing microorganism. Optionally, the nutrient medium may include a gelling agent that assists in "encapsulating" the growing microorganisms. Such gelling agents are known to those of skill in the art, and include any water-absorbing material that becomes a gel upon addition of an aqueous liquid.

Alternatively, one or both of the selective nutrient growth media and the indicator substance may be present as a coating or other deposition within a liquid-retaining zone, in amounts sufficient to achieve desired concentrations when a microvolume of the liquid test sample is distributed into the zone. Such a coating may be achieved, for example, by placing or distributing a solution of the nutrient medium (with or without gelling agent) and/or indicator substance into the liquid-retaining zone and drying the solution to produce a coating or deposition of the nutrient medium and/or indicator substance in the zone. For devices in which the liquid-retaining zones include discs, components of the media may be present in the adhesive or other substance that binds the discs (if applicable) to the substrate. The media ultimately diffuses into the disc material.

A wide variety of selective growth media for a wide variety of microorganisms of interest is known, as is a wide variety of indicator substances for a wide variety of microorganisms, and any of these media or indicator substances is suitable for use in the method of the invention. An advantage of the present invention is that soluble indicators can be used, since diffusion is prevented by confinement of the aqueous biological sample liquid in the hydrophilic liquid-retaining zones.

Various methods may be employed to distribute a liquid test sample to the liquid-retaining zones. More than one method may be applicable to a particular device, although the preferred method may depend to some extent on the configuration of a particular assay device. For example, for film devices containing hydrophilic microvolume wells or for devices in which the zones comprise hydrophilic discs projecting from the plane of the assay surface, the sample may be poured or pipetted over the device and the sample spread to the liquid-retaining zones by tilting or rocking the device. The hydrophilic/hydrophobic interaction acts to retain the sample on the discs and substantially excludes the sample from the substrate.

Alternatively, the assay surface of the device can be immersed in the sample as described in Example 4. Upon removal of the assay surface from the liquid sample, liquid is retained in the hydrophilic liquid-retaining zones and is likewise substantially excluded from the hydrophobic land area.

After the sample is distributed to the hydrophilic liquid-retaining zones of the assay device, various assays may be carried out depending on desired uses. For microbial detection or enumeration, the assay device may be incubated for a time sufficient to permit at least one cell division cycle of the microorganism. For these purposes, the device is generally incubated at about 25° C. to about 45° C., more preferably at about 30° C. to about 37° C. The incubation time for bacterial detection will vary. The detection time for most bacteria will range from about 20 minutes to about 24 hours in order to produce detectable growth as demonstrated by the indicator substance in the incubated liquid test sample. Detection time may vary depending on the growth rate and the number of microorganisms present in the sample. Taking into account these considerations, detection time for purposes of enumeration may be as little as about 10 hours. This relatively short incubation time represents a distinct advantage over detection methods currently used, which typically require incubation times of about 24 hours or more.

Following incubation of the assay device, the presence or absence of the microorganism in the liquid-retaining zones (and thus in the liquid test sample) is detected. The mode of detection depends on the type of indicator substance used in the method. Any indicator substance that is capable of providing a detectable signal may be used. Such indicators include but are not limited to fluorescent, chromogenic, luminescent, and electrochemical indicators. The presence or absence of a microorganism in a zone can be visually detected, with the naked eye or microscopically, if a chromogenic or luminescent indicator is used. When the liquid-retaining zones include discs, the indicator may be coated or otherwise incorporated into the discs. The indicators may also be included in the adhesive or other substance that binds the discs (if applicable) to the substrate. In this instance, the indicator ultimately diffuses into the disc material. If a fluorescent indicator substance is used, equipment and methods for detecting a fluorescent signal may be employed for detection. There are numerous indicator substances and signal detection systems, including systems for detecting electrochemical changes, known in the art for detecting microorganisms. Any such substance or system may be used in accordance with the present invention.

Fluorescent indicators are useful in the method of the present invention because they may be detected at relatively low concentrations. Suitable indicators include 4-methylumbelliferyl phosphate and 4-methylumbelliferyl-β-D-glucopyranoside, L-phenylalanine-7-amido-4-methylcoumarin. Others may include 4-methylumbelliferyl acetate and 4-methylumbelliferyl sulfate.

The detection of microorganisms in the liquid sample may further involve the enumeration of a microorganism count in the liquid test sample. In a preferred embodiment, the enumeration is performed using MPN. Once the number of liquid-retaining zones containing the microorganism of interest is determined, an MPN calculation can be made using known MPN techniques. If desired, the number of microorganisms in an individual zone can then be determined using known techniques, for example, signal intensity compared to a known standard, or by plating the contents of the zone. Advantageously, the large number of liquid-retaining zones used in the method of the invention allows for narrower intervals for the 95% confidence limits in an MPN analysis of a liquid test sample.

Because of the large number of liquid-retaining zones that may be manufactured in a single device, it is possible to use a single device in the detection and enumeration of multiple microorganisms of interest, while retaining the advantages of the invention. For example, a single liquid test sample can be tested for the presence or concentration of $E.$ $coli$ and $S.$ $aureus$. One portion of an assay device can contain hydrophilic liquid-retaining zones for the detection and enumeration of one of these microorganisms, while a second set of zones can be directed to detection and enumeration of another microorganism of interest. This is accomplished, for example, by including microorganism-specific nutrients and/or indicator substances in the respective sets of liquid-retaining zones. Alternatively, all liquid-retaining zones can contain assay reagents designed for the simultaneous detection of multiple microorganisms. For example, $E.$ $coli$ can be detected with a fluorescent indicator substance while, at the same time, other coliforms are detected with a chromogenic indicator substance.

When the liquid-retaining zone include discs, subsequent tests may be conducted. For example, the discs can be removed from the device and transferred into a test tube in order to differentiate the specific microorganisms growing thereon.

In another embodiment, the distribution step can involve distributing aliquots of the liquid test sample to a plurality of hydrophilic liquid-retaining zones of an assay device, wherein the assay device includes a plurality of sets of zones. Each set has zones of uniform size, and the device has at least two sets of zones. For example, the assay device can include a plurality of lanes, with the hydrophilic liquid-retaining zones in a particular lane having the same liquid-retention capacities. Alternatively, the assay device may have a plurality of hydrophilic discs, as described more fully below. Disc volumes may be constant within a set, but may vary between sets. Whether the device has a plurality of lanes or a plurality of disc sets, the liquid test sample may be distributed into different test volume sizes within a single assay device. In MPN, this feature provides a significant advantage in that, for a highly concentrated sample, an appropriate volume size may be selected and MPN analysis performed using a single distribution step in a single device without the need for serial dilutions.

As stated above, the methods of this invention may be practiced using any assay device containing hydrophilic liquid-retaining zones and a hydrophobic land area, depending on the particular embodiment being practiced. The present inventors have developed several novel devices suitable for use in the methods of this invention. The following are non-limiting examples of such devices.

Referring to FIG. 1, a device 10 comprises a substrate 12 having a plurality of hydrophilic liquid-retaining zones in the form of hydrophilic microvolume wells 14. The substrate 12 can be fabricated from any material in which microvolume wells can be fashioned and in which the microvolume wells retain their respective shapes throughout the useful life span of the device 10. Substrate 12 can be fabricated, for example, from polymeric films or other appropriate materials. Appropriate polymers include without limitation polyethylene, polypropylene, polyimides, fluoropolymers, polycarbonates, polyurethanes, and polystyrenes. Should a particular polymer not be sufficiently hydrophilic, it can be treated to impart hydrophilicity. For example, a surfactant can be included in the film to impart hydrophilicity. Those skilled in the art will recognize other means to impart surface hydrophilicity. Microvolume wells 14 can be formed by any process appropriate to the substrate 12 material. Such processes include without limitation thermal embossing, cast embossing, laser drilling, etching with reactive materials, or lamination of a sheet of patterned material containing a plurality of small openings onto a support film. Polyethylene or polypropylene films can be, for example, pressed embossed or extrusion embossed, and can include various pigments and surfactants.

Referring again to FIG. 1, the area 13 between microvolume wells 14 ("land area") is fabricated to be hydrophobic. This serves to prevent aqueous liquid from bridging between the microvolume wells 14, thereby preventing cross-contamination. The land area 13 can be rendered hydrophobic in various ways. For example, the land area on an extrusion embossed polyethylene film, that had been rendered hydrophilic by incorporation of a surfactant, can be rendered hydrophobic by transferring a thin layer of acrylated silicone or other hydrophobic material to the land area. Those skilled in the art will recognize other means to impart surface hydrophobicity.

Figure 2:
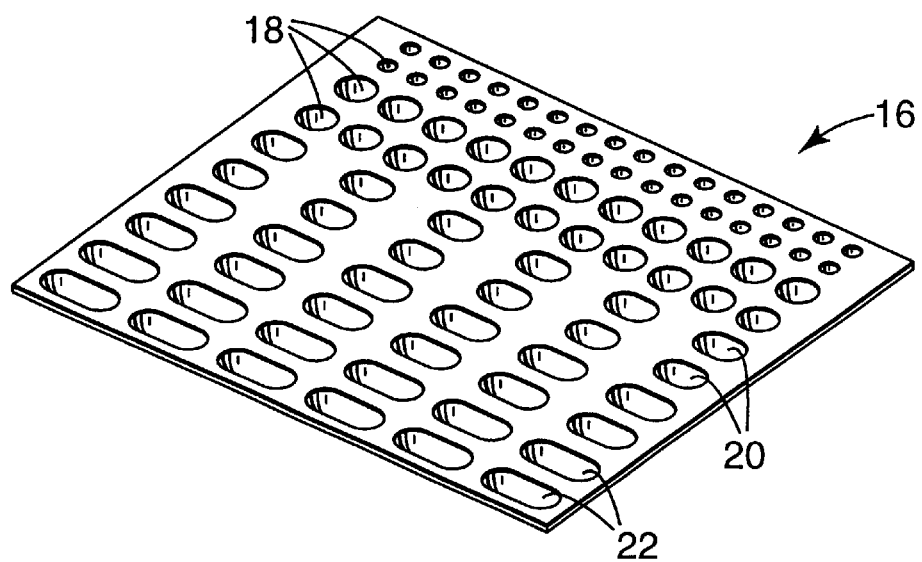
FIG. 2 is a perspective view of an assay device having sets of hydrophilic liquid-retaining zones varying in microvolume capacity of liquid retention.

The device 10 can include any desired number of microvolume wells. Additionally, the device 10 can include relatively large reservoirs or other compartments adapted to hold larger volumes of liquid for maintenance of an appropriate humidity level within the device. Although the number of microvolume wells can be relatively small (e.g., 2–50) for certain applications such as preliminary screening, the small sizes of the microvolume wells allow relatively large numbers of wells to be fabricated on a single device 10. Preferably, the device has about 10 to about 10,000 liquid-retaining zones, even more preferably about 200 to about 5,000 zones, and most preferably about 400 to about 600 zones. The device 10 can have a population of uniformly sized microvolume wells 14 or wells of differing sizes. For example, a device 16 as depicted in FIG. 2 can have sets (e.g., rows) of microvolume wells in which volumes are constant within a set, but vary between sets. As depicted in FIG. 2, the volumes can vary incrementally over an array of sets of wells, with the smaller wells 18 holding sub-microliter volumes and the larger wells 20 holding microliter volumes. It is even possible for the largest wells in a device such as depicted in FIG. 2 to include wells 22 that would not be classified as "microvolume" wells. Such wells might have a liquid-retention capacity, for example, of substantially more than 25 microliters.

In an alternative embodiment, the substrate 12 can be coated with a hydrophobic nanostructured film. For example, polyimide or fluoropolymer webs can be vapor coated with organic pigments, lead, gold and other materials to create specific nanostructured films, then made hydrophobic by coating with an organized molecular assembly, such as octadecyl mercaptan or a fluorocarbon-hydrocarbon thiol, as described in Patent Application WO 96/34697. Relatively hydrophilic microvolume wells and other liquid-retaining zones may be fashioned by removing the hydrophobic nanostructured elements from selected areas of the substrate 12. This can be accomplished in various ways, including without limitation encapsulation/delamination and laser ablation as described in Example 3, below.

Figure 3:
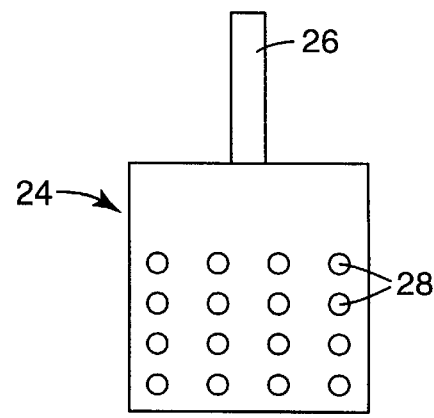
FIG. 3 is a schematic representation of an assay device including a hydrophobic nanostructured film.

A representative hydrophobic nanostructured film device 24 is depicted schematically in FIG. 3. Such devices can be loaded with sample simply by dipping in an aqueous sample solution. To this end, the device 24 can include a handle 26. Handle 26 allows an operator to place the device 24 in a liquid sample to any desired depth up to and including total immersion of the device 24 in the liquid sample, while avoiding contact of the operator's fingers with the sample. Upon removal of device 24 from the sample, liquid sample remains attached to the device only at the locations of the hydrophilic liquid-retaining zones 28. Incubation and detection are then performed as described above.

Assay devices also can be manufactured with hydrophilic liquid-retaining zones constructed of hydrophilic absorbent materials arrayed on a hydrophobic surface. For example, the zones may have a plurality of absorbent discs having circular, oval, square, polygonal or other appropriate shapes. Discs may be constructed from a variety of materials, including cellulosics, polyolefins, polyesters, and polyamides. Suitable cellulosics include paper, wood pulp and rayon and may include chemically modified cellulosics, such as cellulose esters. Suitable polyolefins include hydrophilic polyethylene or hydrophilic polypropylene fibers. Suitable polyamides include nylon. Suitable polyesters include polyactic acid.

Figure 4:
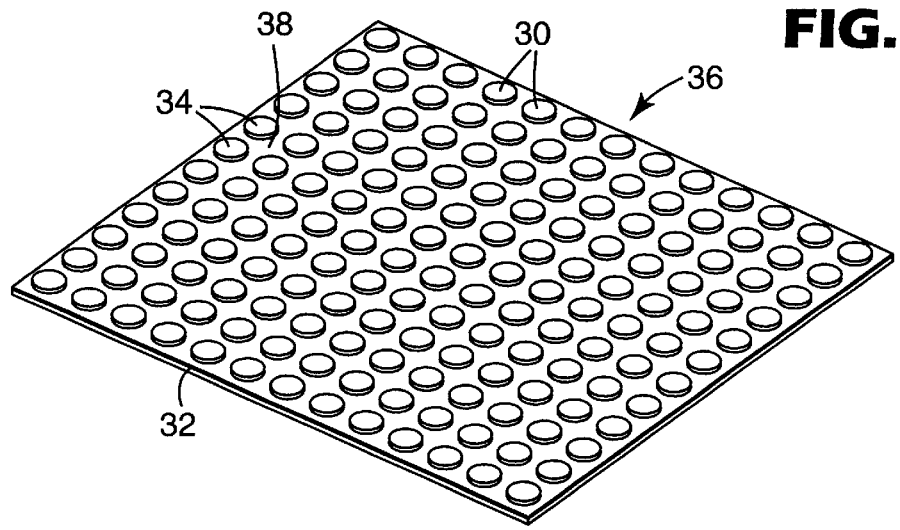
FIG. 4 is a schematic representation of an assay device in which the hydrophilic liquid-retaining zones are constructed of paper discs.

In the device 36 illustrated in FIG. 4, for example, discs of cotton linter binderless paper 30 can be laminated to a silicone-coated film 32 to form hydrophilic liquid-retaining areas 34 that project from the plane of the surrounding hydrophobic surface 36. When present, discs 30 may be attached to the substrate 32 by various means known in the art, including without limitation, by using adhesives. Preferred adhesives include water-insoluble isooctyl acrylate adhesives as disclosed in U.S. Pat. No. 5,409,838. The area between the discs 38 is fabricated to be hydrophobic. This serves to prevent aqueous liquid from bridging the between discs 30, thereby preventing cross-contamination. The area between the discs 38 may be rendered hydrophobic in any manner described above with respect to devices having microvolume wells.

The device can include any desired number of discs 30. Additionally, the device can include relatively large reservoirs or other compartments adapted to hold larger volumes of liquid for maintenance of any appropriate humidity level within the device. As described above with respect to devices comprising microvolume wells, the devices may have a relatively small number (e.g., 2–50) of discs for certain applications. Alternatively, the small sizes of the discs allow relatively large numbers of discs to be affixed to a single device. A single device may have as many as about 10,000 discs.

Figure 5:
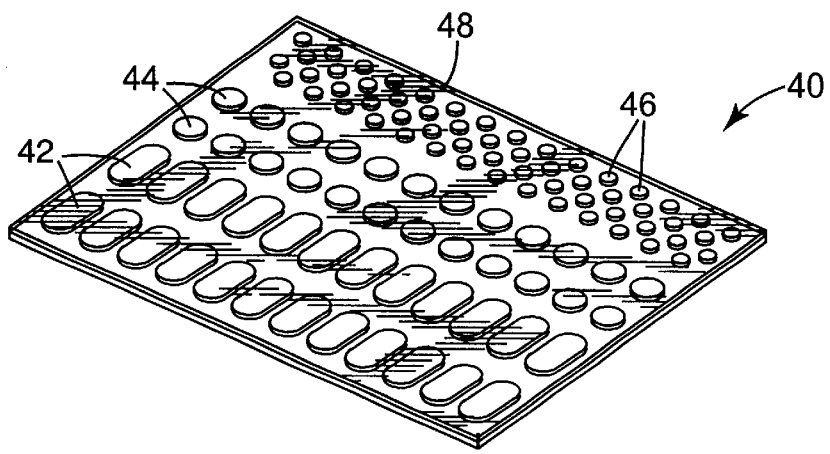
FIG. 5 is a perspective view of an assay device having two sets of different volume discs and a coversheet.

As shown in FIG. 5, the device can have a population of uniformly sized discs or the discs may be of differing sizes. For example, a device 40 may have sets (e.g., rows) of discs in which volumes are constant within a set, but vary between sets. For example, a certain embodiment can have 100 discs in which 50 discs have a volume of 2 microliters and 50 discs have a volume of 20 microliters. Other embodiments may have volumes that vary incrementally over an array of sets of discs, with smaller discs 46 holding sub-microliter volumes and larger discs 44 holding microliter volumes. The largest discs 42 may even have liquid-retention capacities exceeding 25 microliters.

The materials of embodiments of the present invention that include discs are biocompatible and may be used with fluorescent indicators. The materials do not exhibit significant inherent fluorescence that would interfere with the use of indicators. In addition, the discs do not exhibit significant absorption at the emission wavelength of the indicators. Also, the film substrate should not exhibit fluorescent or light-absorbing properties that would interfere with any fluorescent indicator system that is used.

Optionally, the device may include a coversheet 48 to protect the discs from contamination or desiccation once the sample has been added to the device. The coversheet 48 may further be sealed to the device along its edges with a pressure sensitive adhesive.

Figure 6:
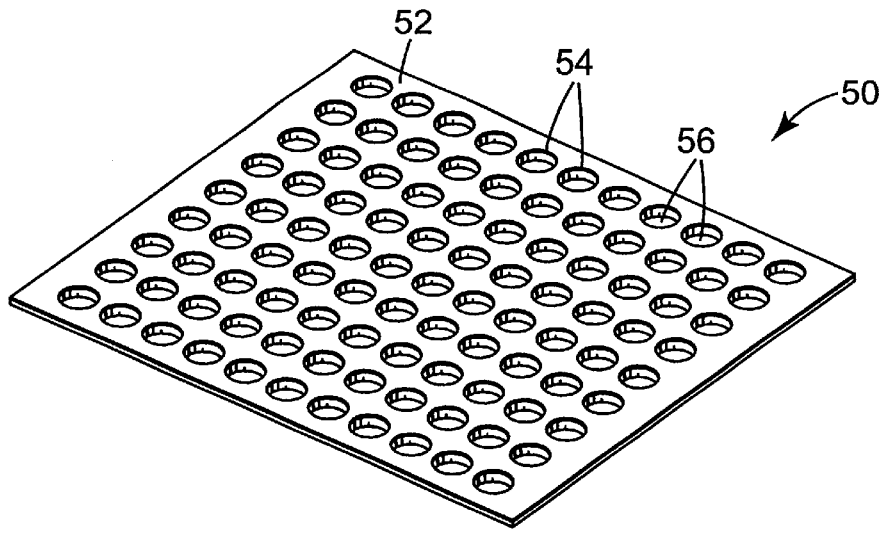
FIG. 6 is a perspective view of an assay device having discs within wells.

In an alternative embodiment, as depicted in FIG. 6, the device 50 may include discs 56 contained in microwells 54 that have been made in the substrate 52 of the device. As with other embodiments, the numbers and size of the discs may be varied.

Figure 7A:
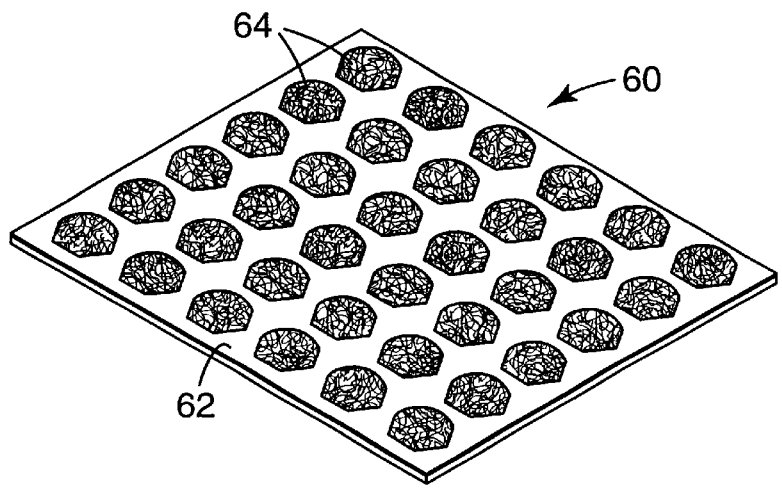
FIG. 7a is a perspective view of an assay device in which the hydrophilic liquid-retaining zones are constructed of nonwoven fiber loop material.
Figure 7B:
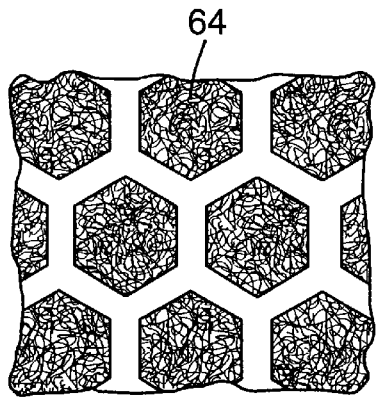

Alternatively, the hydrophilic liquid-retaining zones may be constructed of nonwoven fiber loop material that likewise protrudes (projects) from the plane of the surrounding hydrophobic land area. For example, as illustrated in FIGS. 7a and 7b, the assay device 60 may comprise a sheet of hydrophobic polypropylene film 62 containing arrays of protrusions 64 fabricated from surfactant-containing polypropylene nonwoven fiber loop material.

Assay reagents can be coated or otherwise deposited within the liquid-retaining zones of the assay devices. Such assay reagents can include without limitation nutrients for growth of microorganisms; gelling agents; indicator substances such as chromogenic indicators, fluorescent indicators, luminescent indicators, and electrochemical indicators. The assay reagents can be immobilized in the liquid-retaining zones by any of numerous methods for immobilizing assay reagents on solid substrates known to those of skill in the art. Such methods include for example drying down assay reagent-containing liquids in the zones, as well as other methods for noncovalently attaching biomolecules and other assay reagents to a solid substrate. Alternatively, various methods may be employed to covalently attach assay reagents to the substrate 12 material within the wells 14 by methods well known to those of skill in the art.

As discussed above, the presence of hydrophilic liquid-retaining zones with microvolume liquid-retention capacity in an assay device allows for separation of a liquid test sample into a relatively large number of test volumes. The ability to separate a liquid sample into microvolume aliquots and to perform MPN or other assays without cross-contamination between aliquots is an advantage of the present method and devices.

All references and publications cited herein are expressly incorporated herein by reference into this disclosure. Particular embodiments of this invention will be discussed in detail and reference has been made to possible variations within the scope of this invention. There are a variety of alternative techniques and procedures available to those of skill in the art that would similarly permit one to successfully practice the intended invention.

EXAMPLES

The following examples are offered to aid in understanding of the present invention and are not to be construed as limiting the scope thereof. Unless otherwise indicated, all parts and percentages are by weight.

Example 1

Embossed Film Culture Devices

Embossed film culture devices containing a plurality of microcompartments and capable of being used for the detection of microorganisms in a liquid test sample were constructed as described in this example.

The hydrophilic liquid-retaining zones can be formed in a substrate by a number of processes, examples of which are thermal embossing, cast embossing, laser drilling, and by etching the surface with a reactive material. Detailed descriptions of how to make recesses or microvolume wells in polymeric films are provided in U.S. Pat. Nos. 5,192,548; 5,219,462; 5,344,681; and 5,437,754. The following descriptions are representative of specific embossed film culture devices used in the subsequent examples.

A. Pressed Embossed Films Containing a Plurality of Microvolume Wells

Polyethylene (Eastman Chemical Company Resin #18BOA) containing 10% by weight $TiO_2$ (50% $TiO_2$/50% Polyethylene Pigment Concentrate) and 0.5% by weight Triton X-35 Surfactant (Sigma Chemical Company) or polypropylene was extrusion cast into a film (4-mil thickness). The film was cut into sheets and stacked (~20 sheets) onto photolithographically etched magnesium alloy tooling as described in U.S. Pat. No. 5,219,462, designed to form a plurality of microvolume wells. The etched magnesium tooling contained protuberances arranged in the patterns described in subsequent examples. The stacked polyethylene sheets were embossed on a heated hydraulic press (132° C., 1.4 $N/m^2$, 120 second dwell) as described in U.S. Pat. No. 5,219,462. The samples were allowed to cool, at which time the tooling was removed to provide a single layer film containing the "negative" image of the tooling.

B. Extrusion Embossed Films Containing a Plurality of Microvolume Wells

Photolithographically etched magnesium master tooling was attached to a steel roll using pressure-sensitive transfer adhesive. The polyethylene, pigment, and surfactant composition described in Example 1A was blended together and extrusion cast onto the roll as described in U.S. Pat. No. 5,192,548. Embossed films lacking the Triton X-35 surfactant were also prepared in this manner.

C. Extrusion Embossed Films with Hydrophobic "Land" Area

Extrusion embossed polyethylene films containing Triton X-35 Surfactant were prepared according to Example 1B. The area between microvolume wells ("land" area) was rendered hydrophobic by transferring a thin layer of acrylated silicone (Goldschmidt FC 711) containing 4.8% of a cross linking agent (Darocur 1173) with a roll-to-roll coating apparatus (Straub Design Co.). The hydrophobic coating was cured by exposing the film to ultraviolet radiation under nitrogen atmosphere using a Fusion Systems UV lamp with an H bulb providing a dosage of 85 millijoules/$cm^2$.

Example 2

Method of Inoculation (Method Utilizing Plurality of Microvolume Wells)

A. Inoculation with Indicator Solution

An aqueous solution containing phenol red indicator (to provide contrast) was applied by pipette onto silicone-treated and silicone-untreated polyethylene embossed films (Examples 1C and 1B, respectively) containing a plurality of microvolume wells (about 1.3 $\mu$l/well). The microvolume wells were arranged in a hexagonal array (~19 wells/$cm^2$) and each well was in the shape of an inverted truncated cone, having a diameter of approximately 1.9 mm at the surface and 1.0 mm at its depth, which was about 1.1 mm. The microvolume wells were filled as described in U.S. Pat. No. 5,219,462 by drawing the diluted sample solution down the film with the edge of a razor blade. The samples treated with the hydrophobic silicone coating were shown to partition liquid into individual microvolume wells without fluid bridging between the wells, whereas bridging of liquid was observed on the untreated films.

B. Inoculation with Microorganism-Containing Samples

The method of inoculating embossed film culture devices containing a plurality of microvolume wells with bacteria-containing media was demonstrated in this example. The inoculated devices were utilized to detect and enumerate *E. coli* bacteria.

Figure 8A:
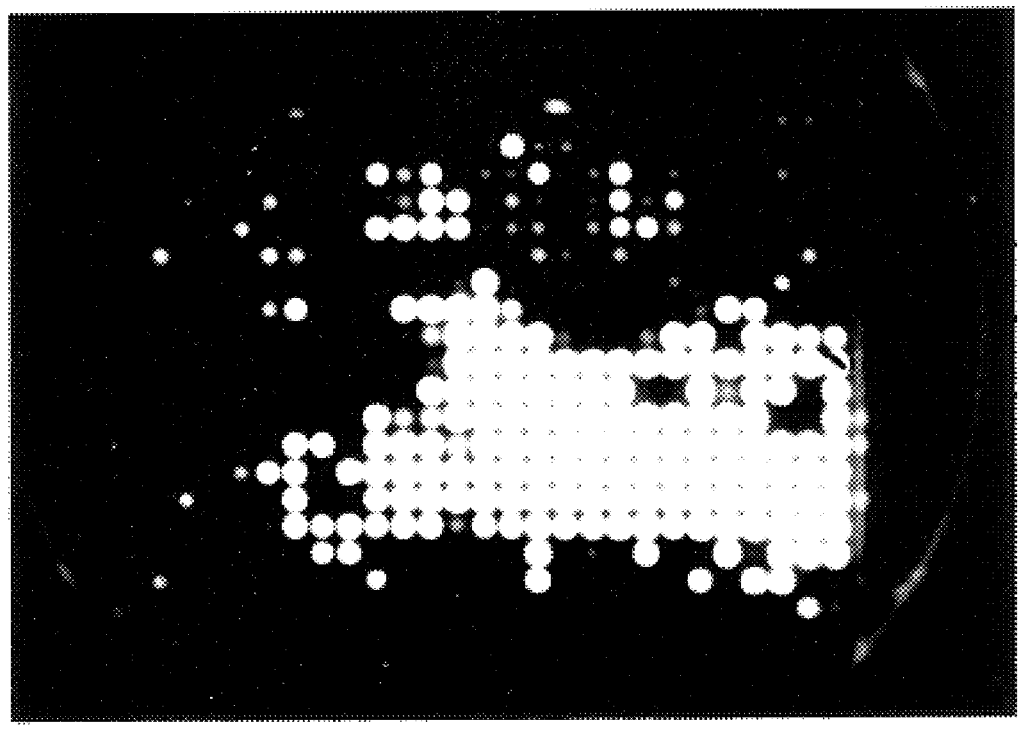
FIG. 8a is a photograph of a top view of an assay device in which the assay surface is hydrophilic.
Figure 8B:
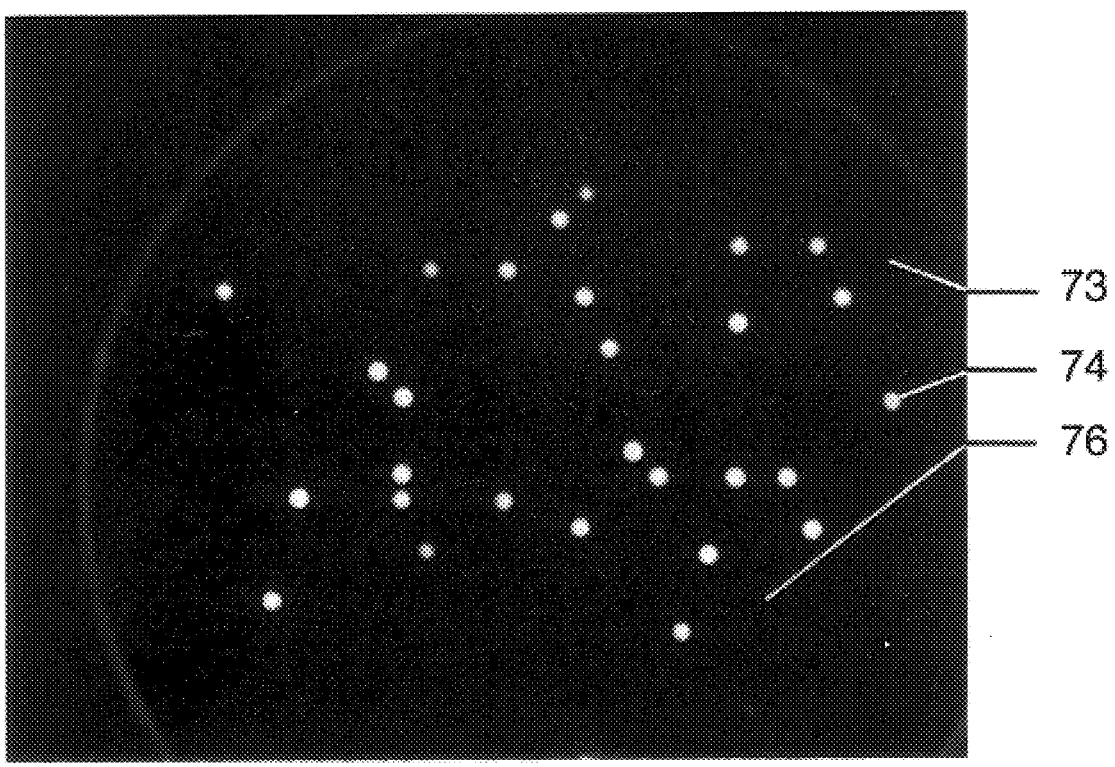
FIG. 8b is a photograph of a top view of an assay device with hydrophilic liquid-retaining zones and hydrophobic land areas.

An overnight broth culture of *E. coli* ATCC 51813 ($\sim 10^9$ CFU/ml in Tryptic Soy Broth (TSB) media) was serially diluted into Violet Red Bile (VRB) media (7.0 g/l Bacto peptone, 3.0 g/l yeast extract, and 1.5 g/l bile salts) containing 4-methylumbelliferyl-β-D-glucuronide (0.5 mg/ml) (MUG, Biosynth International, Naperville, L). The dilution was prepared to the approximate bacterial concentration of 100 CFU/ml. The diluted sample (0.5 ml) was applied by pipette onto silicone-treated and silicone-untreated polyethylene embossed films (406 microvolume wells) as described in Example 2A. The inoculated embossed films 73 were placed inside petri dishes, and incubated for 12 hours at 37° C. Twenty-eight microvolume wells 74 exhibited sharp, discrete fluorescent spots on the silicone-treated film 76 (FIG. 8b). In contrast, significant well-to-well cross-contamination was observed on the untreated film (FIG. 8a). For the silicone-treated film, 28 positive wells corresponds to a most probable number (MPN) of 58 CFU/ml, as calculated using the formula MPN=N 1n (N/N-X) where N is the total number of filled wells and X is the total number of wells showing a positive reaction.

The results of this example show that microorganisms can be readily detected and enumerated using an embossed film culture device having a plurality of microvolume wells and that well-to-well cross-contamination can be eliminated by coating a hydrophobic substance on the land area between wells.

Example 3

Nanostructured Film Culture Devices

Nanostructured film culture devices containing a plurality of hydrophilic microvolume liquid-retaining zones arrayed on a substrate coated with a hydrophobic nanostructured film were constructed as described in this example.

A. Nanostructured Film

Processes for generating nanostructured surfaces are disclosed in U.S. Pat. Nos. 4,812,352 and 5,039,561. Briefly, the organic pigment C.I. Pigment Red 149 (American Hoechst-Celanese, Somerset, N.J.) was vacuum vapor deposited to a thickness of 250 nm onto a 0.0125-nm thick, 30×30 cm sheet of polyimide web, which had previously been metal vapor coated with 700 Å of lead. The sample was annealed in a vacuum oven at 264° C. for greater than 30 minutes, which was sufficient to convert the PR 149 pigment to a dense distribution of discrete crystalline whiskers oriented perpendicular to the web substrate. The whiskers were vapor coated with a mass equivalent thickness of 2500 Å of gold, which resulted in a conformational coating of gold particles, $\sim 2\,\mu m$ tall and $\sim 0.15$ mm in diameter, with an areal number density of 5 per $(\mu m)^2$, as determined by SEM.

Alternatively, the polyimide was replaced with a transparent fluorenone polyester (FPE, 3M Co.) and vapor coated with 50 Å of gold, which prevented surface charging during deposition of the PR 149, yet remained essentially transparent.

B. Hydrophobic Nanostructured Film

The nanostructured film was then made hydrophobic by immersing in a 0.1 mM solution of $C_8F_{17}(CH_2)_{11}SH$ in ethanol for 4 hours, followed by rinsing with pure ethanol and air drying. The resulting highly hydrophobic surface was measured to have identical advancing and receding contact angles of 178° for water. This process is described in Patent Application WO 96/34697.

C. Nanostructured Film Culture Devices

Nanostructured film culture devices were constructed by using an encapsulation/delamination of nanostructured films process described in U.S. Pat. No. 5,336,558. Briefly, pieces of the nanostructured hydrophobic film were cut into 1.5× 2.0 cm strips. A 0.25-mm thick perforated steel sheet, having a square array of 1.5-mm diameter holes spaced ~4 mm apart, was laid over the nanostructured side of the strips. A fast curing vinyl polysiloxane encapsulate (3M EXPRESS dental impression material, 3M Co.) was applied liberally over the steel plate to cause the material to penetrate through the holes and encapsulate the nanostructured whiskers. After several minutes, the impression material was set and the steel sheet was removed, thereby removing the nanostructured elements cleanly from the polyimide web only at the location of the array of holes. The exposed metal-coated polyimide substrate in the areas under the holes was relatively hydrophilic compared to the remainder of the surface. This was demonstrated by dipping the strips into an aqueous solution and observing that small droplets remained attached only at the array of exposed spot or zone areas.

Alternatively and preferably, laser ablation was utilized for removing the nanostructured elements from the polyimide web to provide the desired array of relatively hydrophilic liquid-retaining zones. The strips of nanostructured hydrophobic film were ablated with a Nd-YAG laser with a collimated beam 1 mm in diameter and operated in a Q-switched mode with approximately 2 mjoule, 60 nanosecond pulses. Single pulses were used to ablate rows of 1-mm diameter zones on 4- and 5-cm center-to-center spacing. Larger zones, ~1.6×1.6 mm square, were produced by overlapping a 3×3 matrix of nine 1-mm diameter zones. The resulting nanostructured film culture device with 40 (4×10) zones was submersed in water for 1 minute initially to make the ablated zone areas hydrophilic. Upon withdrawing the plate, each of the 40 zones had an ~1-mm diameter, hemispherical droplet attached to it.

Example 4

Method of Inoculation (Method Utilizing Nanostructured Film Culture Devices)

A. Inoculation with Aqueous Liquid Sample

To inoculate and measure the amount of liquid selectively retrieved by the nanostructured film culture devices (Example 3C), a plate with 12 hydrophilic liquid-retaining zones, ranging in size from 1 to 2.5 mm in diameter (average 2 mm), was dipped into pure water and the amount of water extracted onto the zones was measured gravimetrically. The plate was first dipped at a slow withdrawal rate of ~3 seconds/cm. After withdrawal, the back of the plate was touched against tissue paper to remove any water droplets clinging to the back of the polyimide plate, and the plate was then placed on a mass balance (0.1 mg minimum sensitivity) and the mass recorded 15 seconds later. This was repeated 15 times. The mean and standard deviation of the mass of the 12 water zones was 3.7±0.2 mg, giving an average zone volume of 0.310 μl±5%. The procedure was then repeated a fast withdrawal rate with the plate pulled from the water in a time estimated to be ~0.1 second. At this rate, the amount of liquid that remained on the hydrophilic zones was larger, because the liquid did not have time to "stretch" and dynamically equilibrate. The mean and standard deviation of the 15 trials was 6.0±0.5 mg, giving an average zone volume of 0.500 μl±12%.

B. Inoculation with *S. Aureus*-Containing Samples

The method of inoculating nanostructured film culture devices containing a plurality of microvolume liquid-retaining zones with bacteria-containing media was demonstrated in this example. The inoculated devices were utilized to detect and enumerate *S. aureus* (Example 4B) and *E. coli* (Example 4C) bacteria.

A mixture (5 μl) of molten (~60° C.) bacteriological growth media BHI (Brain Heart Infusion, Becton Dickinson and Co.) and agar (1.2% weight/volume) was spotted onto the hydrophilic zones of the nanostructured film culture devices prepared as described in Example 3C. The agar "spots" were allowed to cool and solidify at room temperature. One plate was dipped briefly into a growing culture of *Staphylococcus aureus* (~$10^8$ cells/ml) in BHI broth medium. Other plates were dipped similarly into 1:10 and 1:1000 dilutions of the *S. aureus* culture, representing $10^7$ and $10^5$ cells/ml, respectively. The plates were placed into plastic petri dishes containing water-saturated filter paper to maintain humidity, and incubated at 37° C. for 4 hours. The plates were then dipped into a solution containing 900 μl of HEPES Buffer (Sigma Chemical Co., pH 8.0); 120 μl of fluorescent indicator solution (1.0 mg/ml Boc-Val-Pro-Arg-AMC HCl (NovaBiochem, San Diego, Calif.) in 72 mM triethanolamine, 144 mM NaCl, pH 8.4); and, 30 μl human prothrombin (Sigma Chemical Co., 50 mg/ml in 5 mM Tris buffer, 50 mM NaCl, pH 8.0). The plates were incubated for one additional hour under the same conditions described above and then examined under UV light (~366 nm, Mineralite, UVP, Inc., San Gabriel, Calif.). The zones containing agar media, bacterial suspension, and indicator solution all showed visible, intense bluish fluorescence as compared to no visible fluorescence in the control samples, which were prepared without any added bacteria. No cross-contamination between zones was observed.

C. Inoculation with *E. coli*-Containing Samples

Agar medium was prepared by combining the following ingredients: pancreatic digest of gelatin (10 g, Peptone G, Acumedia Manufacturers, Inc., Baltimore, Md.); Bacto Bile Salts Number 3 (2.5 g, Difco Labs, Detroit, Mich.); Agar (6 g, Difco Labs); and deionized water (500 ml). The mixture was stirred and heated to 100° C. until the agar melted, autoclaved at 121° C. for 15 minutes to sterilize, and then cooled to room temperature to solidify. An IPTG stock solution was prepared from filter-sterilized (0.2 mm) isopropyl-β-D-galactoside (IPTG, CalBiochem Corp., La Jolla, Calif.) in deionized water (200 mg/ml) and stored at −20° C. until use. A MU-Gal stock solution was prepared from 4-methylumbelliferyl-β-D-galactoside (MU-Gal) in N,N-dimethylformamide (10 mg/ml) and stored at 4° C. until use. Immediately before use the agar medium was melted at 100° C. and 25 ml was transferred to a sterile 50-ml tube. The IPTG stock solution (12.5 ml) and the MU-Gal stock solution (150 mil) were then mixed into the cooled (~60° C.) agar suspension. The mixture was immediately transferred (4-μl aliquots) to the nanostructured film culture device zones as described in Example 4B. After cooling to room temperature, the plates were dipped into a mid-exponential growing culture of *E. coli* ATCC 51813 (~$10^8$ cells/ml in LB medium 3) and incubated in individual humidified petri dishes at 37° C. After 4 hours of incubation, the plates were checked for fluorescence with a Mineralite UV lamp. The inoculated zones exhibited slightly more fluorescence than that observed in the uninoculated zones. The plates were then incubated for an additional 16 hours and rechecked. The inoculated zones showed significantly more blue fluorescence than the uninoculated zones. The plate prepared with clear-film substrate (Example 3A utilizing FPE) was particularly convenient to measure because it could be illuminated from one side and viewed or photographed from the other side. No cross-contamination between zones was observed.

Example 5

Absorbent Disc Culture Devices

Absorbent disc culture devices containing a plurality of hydrophilic absorbent discs arrayed on a hydrophobic surface and capable of being used for the detection and enumeration of microorganisms in a liquid test sample were constructed as described in this example.

A. Culture Devices Constructed with Absorbent Paper Discs

A sheet of absorbent material (Schleicher & Schuell Grade 903 Paper; absorbs about 4.5 g of water/100 $cm^2$) was laminated to a Rexam silicone-coated film (Grade #15819 D 2MIL CL PET MM34P/000 having a clear 2-mil thick polyester film as a substrate, Rexam Release, Oak Brook, Ill.) with an acrylate pressure sensitive adhesive (PSA) containing the chromogenic indicator 2,3,5-triphenyl-2H-tetrazolium chloride (TTC) (Amresco, Solon, Ohio). The material was saturated with tryptic soy broth (TSB) growth nutrient containing 0.5% of the fluorescent indicators 4-methylumbelliferyl phosphate (100 μg/ml, Sigma, St. Louis, Mo.) and 4-methylumbellifery-α-D-glucoside (50 μg/ml, Sigma), wiped with a wire-wound rod, and dried at 110° C. for 10 minutes. Circular discs approximately 0.635 cm in diameter were punched out of the laminate and the silicone-coated film backing removed. The discs with PSA were then adhered to another sheet of Rexam silicone-coated film so that the discs were patterned in equally spaced parallel rows. The film and discs that the discs were patterned in equally spaced parallel rows. The film and discs assemblies were gamma irradiated to a level of 8.9 kGy, cut to size, and then taped into a petri dish such that each dish contained a piece of film with 20 discs. Based on gravimetric measurements, each disc in the resulting culture devices had a capacity to retain about 40 μl of liquid.

B. Culture Devices Constructed with Various Polymeric Absorbent Disc Materials

Silicone-coated polyester release liner (as described in Example 5A) and biaxially-oriented polypropylene (BOPP) film (1.6-mil thickness, 3M Co., St. Paul, Minn.) were cut into 7.6-cm×10.2-cm rectangular pieces. Pieces of each material were joined at one end with SCOTCH™ brand double-coated adhesive tape (No. 665, 3M Co.) with the silicone-coated side of the release liner oriented toward the BOPP film. The release liner functioned as the base of the culture device and the BOPP film functioned as the top film.

Sheets of the following polymeric absorbent materials were laminated onto separate layers of an acrylate adhesive (No. Y966, 3M Co.): Product No.10201-9 cellulose (Dexter, Windsor Locks, Conn.), Grade 903 cotton lint paper (Schleichter & Schuell, Keene, N.H.), Product No. P-110 Supersorbent polyolefin (3M Co.), Product No. 9208283 polyester (Veratec, Walpole, Mass.), Spunbond Nylon (4 ounces per square yard) polyamide (Cerex Advanced Fabrics, Cantonment, Fla.), and polylactic acid polyester [absorbent nonwoven meltblown web prepared from polylactic acid pellets (HEPLON™, Chronopol, Inc., Golden, Col.) as described in U.S. Pat. No. 5,230,701]. Circular discs (approximately 0.64-cm diameter) were punched out of the resulting laminates and adhered to the silicone-coated side of the polyester release liner. Each culture device contained 12 discs equally spaced in a 3×4 array of parallel rows. After construction was completed, the culture devices were gamma irradiated to a level of 8 kGy. Each disc had the capacity to retain about 10 µls.

Example 6

Method of Inoculation (Method Utilizing Absorbent Disc Culture Devices)

The method of inoculating absorbent disc culture devices containing a plurality of microvolume liquid-retaining zones (absorbent discs) with bacteria-containing media was demonstrated in this example. The inoculated devices were utilized to detect and enumerate E. coli bacteria.

A. Microbial Assay Using Culture Devices Constructed with Absorbent Paper Discs (from Example 5A)

A culture of E. coli ATCC 51813 was diluted to produce suspensions containing about 10 CFU/ml and 1 CFU/ml. Samples (1 to 2 ml) of the suspensions were applied by pipette to the absorbent disc culture devices described in Example 5A. Excess liquid sample was poured off, thereby leaving about 0.8 ml retained on the device (20 discs, about 40 µl of liquid per disc). The inoculated devices were incubated at 35° C. for 23 hours and inspected under ultraviolet light. The number of discs exhibiting fluorescence was counted for each device and most probable number (MPN) values calculated using the formula described in Example 2B. The MPN per milliliter was calculated by dividing the value obtained by the total volume of the sample (0.8 ml). Results are provided in Table 1 and are compared with counts obtained from standard testing with Coliform Count PETRIFILM™ Plates (3M Co.). The fluorescent discs often showed the red TTC color, usually as discrete spots within the discs. No cross-contamination between absorbent discs was observed.

TABLE 1

Enumeration of Microorganisms (E. coli)

| Bacterial Suspension (- CFU/ml) | Positive Discs (Out of 20) | MPN (CFU/ml) | Coliform Count PETRIFILM ™ |
|---|---|---|---|
| 10 | 17 | 47 | 22 |
| 10 | 19 | 74 | 24 |
| 1 | 2 | 2.6 | 5 |
| 1 | 3 | 4.1 | 4 |

The results of this example show that absorbent disc culture devices having a plurality of absorbent discs arrayed on a hydrophobic film can be easily inoculated with bacteria-containing liquid samples and that the inoculated devices can be utilized for the detection and enumeration of E. coli, with the values obtained being comparable with those obtained from commercial Coliform Count PETRIFILM™ Plates.

B. Microbial Assay Using Culture Devices Constructed with Various Polymeric Absorbent Disc Materials (from Example 5B)

Cultures of different bacterial strains (Table 2) were grown overnight at 35° C. in 5 ml of TBS media. A 0.01-ml volume of each culture was diluted into 99 ml of sterile Butterfield's diluent (Fisher Scientific, Pittsburgh, Pa.), to obtain initial $10^{-4}$ dilutions of the original bacterial suspensions. Three subsequent 10-fold dilutions ($10^{-5}$, $10^{-6}$, and $10^{-7}$) of the bacterial suspensions were made in Standard Methods Broth containing the following ingredients: Pancreatic Digest of Casein (10.0 g/l, Difco Labs), Yeast Extract (5.0 g/l, Difco Labs), Glucose (2.0 g/l, Becton Dickinson and Co., Cockeysville, Md.), and the fluorescent indicator 4-methylumbelliferylphosphate (0.05 g/l, Biosynth International). With the top covers of the culture devices (from Example 5B) raised, three 0.01-ml aliquots of the $10^{-5}$, $10^{-6}$, and $10^{-7}$ dilutions were transferred by pipette onto nine individual discs on each of the devices. An equivalent volume of sterile medium was transferred to the remaining three discs on each device to serve as sterility controls. The top covers of the inoculated culture devices were closed, and the devices placed into GLAD-LOCK® ZIPPER™ storage bags (First Brands Corp., Danbury, Conn.), each containing a moistened paper towel. The bags were placed in a 35° C. incubator for 24 hours, after which the culture devices were examined under a long-wave ultraviolet light source. Positive growth and detection was evidenced by a bluish fluorescence. Results are provided in Table 2.

TABLE 2

Growth and Detection of Bacteria on Various Disc Materials

| Bacterial Strain | Disc Material | No. of Positive Discs (at designated dilutions) | | | |
|---|---|---|---|---|---|
| | | $10^{-5}$ | $10^{-6}$ | $10^{-7}$ | Control |
| Escherichia coli P18 (Clinical isolate; obtained from Centers for Disease | Cellulose (Dexter) | 3 | 3 | 3 | 0 |
| | Paper (S & S) | 3 | 3 | 3 | 0 |

TABLE 2-continued

Growth and Detection of Bacteria on Various Disc Materials

| Bacterial Strain | Disc Material | No. of Positive Discs (at designated dilutions) | | | |
|---|---|---|---|---|---|
| | | $10^{-5}$ | $10^{-6}$ | $10^{-7}$ | Control |
| Control and Prevention, Atlanta, GA) | Polyolefin (3M) | 3 | 3 | 3 | 0 |
| | Polyester (Veratec) | 0 | 0 | 0 | 0 |
| | Polyamide (Cerex) | 3 | 3 | 3 | 0 |
| Bacillus sp. L11 (Food isolate) | Cellulose (Dexter) | 3 | 3 | 0 | 0 |
| | Paper (S & S) | 3 | 2 | 0 | 0 |
| | Polyolefin (3M) | 0 | 0 | 0 | 0 |
| | Polyester (Veratec) | 0 | 0 | 0 | 0 |
| | Polyamide (Cerex) | 1 | 0 | 0 | 0 |
| | Polylactic Acid Polyester (Chronopol) | 2 | 0 | 1 | 0 |
| Streptococcus faecium P92 (Clinical isolate; obtained from Centers for Disease Control and Prevention) | Cellulose (Dexter) | 3 | 1 | 0 | 0 |
| | Paper (S & S) | 3 | 0 | 0 | 0 |
| | Polyolefin (3M) | 0 | 0 | 0 | 0 |
| | Polyester (Veratec) | 0 | 0 | 0 | 0 |
| | Polyamide (Cerex) | 3 | 0 | 0 | 0 |
| | Polylactic Acid Polyester (Chronopol) | 3 | 1 | 0 | 0 |
| Hafnia alvei 3026 (Obtained from the University of Minnesota) | Cellulose (Dexter) | 3 | 3 | 1 | 0 |
| | Paper (S & S) | 3 | 2 | 0 | 0 |
| | Polyolefin (3M) | 1 | 0 | 0 | 0 |
| | Polyester (Veratec) | 0 | 0 | 0 | 0 |
| | Polyamide (Cerex) | 3 | 1 | 0 | 0 |
| | Polylactic Acid Polyester (Chronopol) | 3 | 3 | 0 | 0 |

The results of this example show that culture discs constructed with an array of discs made from different absorbent materials can be utilized for the detection of various bacterial strains. Especially effective in this example were absorbent discs made from cellulosic, polyamide, and polyolefin materials.

Example 7

Method of Inoculation (Method Utilizing Hydrophilic Fiber Culture Devices)

The method of constructing and inoculating hydrophilic fiber culture devices containing a plurality of microvolume liquid-retaining zones (nonwoven fiber loops) with indicator solution and with bacteria-containing media were demonstrated in this example. The inoculated devices were utilized to detect and enumerate E. coli bacteria.

A. Device Construction

A sheet of hydrophobic polypropylene film containing an array of relatively hydrophilic surfactant-containing polypropylene nonwoven fiber loop protrusions was prepared as described in U.S. Pat. No. 5,256,231. The sheet was cut to size and taped to the bottom of a petri dish to form a culture device. Each device contained film having about 200 fiber loop protrusions patterned hexagonally in equally spaced parallel rows. Each hemispherical protrusion was hexagonal at its base (side length about 3 mm, height about 2 mm) and had a capacity to retain about 15 $\mu$l of liquid.

B. Inoculation with Indicator Solution

A sample (1 ml) of phosphate buffer ("Butterfield", Fisher Scientific) containing phenol red indicator (to provide contrast) was applied by pipette onto the film in the center of the device. The liquid was observed to wick into the hydrophilic fiber loop protrusions radially from the point of inoculation. The liquid was observed to quickly partition into the loop protrusions while "draining" from the hydrophobic polypropylene land areas. About 65 of the 200 protrusions were filled. No bridging of the colored liquid across the land areas between loop protrusions was observed.

C. Inoculation with Microorganism-Containing Sample

An overnight culture of E. coli (ATCC 51813, ~$10^9$ CFU/ml in TSB media) was serially diluted into VRB Media (7.0 g/l Bacto peptone, 3.0 g/l yeast extract, 1.5 g/l bile salts) containing 4-methylumbelliferone-β-D-glucuronide (0.5 mg/ml). A dilution of $10^{-8}$ was prepared corresponding to a bacterial concentration of about 10 CFU/ml. A sample (1 ml) was pipetted onto the film in the center of a hydrophilic fiber culture device (Example 7A) as described in Example 7B. After inoculation, the petri dish was covered and sealed using electrical tape to prevent evaporation. The device was then inverted and incubated at 37° C. for 19 hours. After incubation, the number of protrusions exhibiting fluorescence under 365 nm irradiation were counted. Five separate, discrete protrusions were observed to have significant fluorescence. No fluorescence was observed between protrusions, thereby indicating no cross-contamination. The MPN value was calculated to be 5 CFU/ml, using the formula described in Example 2B.

The results of this example show that hydrophilic fiber culture devices having a plurality of hydrophilic fiber zones arrayed on a hydrophobic film can be easily inoculated with bacteria-containing liquid samples and that the inoculated devices can be utilized for the detection and enumeration of E. coli.

Various modifications and alterations of this invention will be apparent to those skilled in the art without departing from the scope and spirit of this invention, and it should be understood that this invention is not limited to the illustrative embodiments set forth herein.

What is claimed is:

1. A culture device for detection or enumeration of microorganisms, said device comprising a substrate comprising liquid-retaining discs comprising a hydrophilic material, wherein said substrate comprises a material that is hydrophobic relative to said liquid-retaining discs and wherein the discs comprise media for growth of microorganisms.

2. The culture device of claim 1 wherein said discs are constructed at least in part of a material selected from the group consisting of cellulosics, polyolefins, polyamides and polyesters.

3. The culture device of claim 2 wherein the discs are constructed at least in part of alpha cellulose.

4. The culture device of claim 2 wherein the discs are constructed at least in part of rayon.

5. The culture device of claim 2 wherein the discs are constructed at least in part nylon.

6. The culture device of claim 2 wherein the discs are constructed at least in part of polylactic acid.

7. The culture device of claim 1 wherein said device has about 10 to about 10,000 discs.

8. The culture device of claim 1, wherein said device has about 400 to about 600 discs.

9. The culture device of claim 1, wherein each said disc has a liquid retention capacity of about 1 to about 2 microliters.

10. The culture device of claim 1, having an indicator substance on said discs.

11. The culture device of claim 1 wherein the discs are adhered to the substrate with adhesive, and wherein said adhesive has an indicator for detecting microorganisms.

12. The culture device of claim 10, wherein said indicator substance is selected from the group consisting of a chromogenic indicator, a fluorescent indicator, a luminescent indicator and an electrochemical indicator.

13. The culture device of claim 1, wherein said culture device comprises a plurality of at least two sets of liquid-retaining discs, each set comprising discs of uniform size, said sets varying in liquid retention capacity.

14. A method for partitioning an aqueous liquid sample into discrete microvolumes, comprising:
  a) providing a device for culturing a microorganism, said device comprising an assay surface, said surface comprising liquid-retaining discs comprising a hydrophilic material and a land area comprising a hydrophobic material between said discs, each said disc comprising media for growing microorganisms; and
  b) contacting said liquid sample with said assay surface such that said liquid sample is partitioned into said liquid-retaining discs.

15. The method of claim 14, wherein the discs are constructed of a material selected from the group consisting of cellulosics, polyolefins, polyamides and polyesters.

16. The method of claim 15, wherein the discs are coated with a growth medium.

17. The method of claim 14, wherein said discs have at least one indicator substance coated thereon.

18. The method of claim 17, wherein said indicator substance is selected from the group consisting of a chromogenic indicator, a fluorescent indicator, a luminescent indicator and an electrochemical indicator.

19. The method of claim 14, wherein said discs are of uniform size and each said disc has a liquid retention capacity of about 0.01 to about 25 microliters.

20. The method of claim 14 wherein each said disc has a liquid retention capacity of about 1 to about 2 microliters.

21. The culture device of claim 1 wherein at least one of the discs has a microvolume capacity of liquid retention.

22. The method of claim 14 wherein at least one of the discs has a microvolume capacity of liquid retention.

23. A method for partitioning an aqueous liquid sample into discrete microvolumes, comprising:
  a) providing a device for culturing a microorganism, the device comprising an assay surface, the assay surface comprising liquid-retaining zones comprising a hydrophilic material and a land area comprising a hydrophobic material between the zones; and
  b) contacting the liquid sample with the assay surface such that the liquid sample is partitioned into the liquid-retaining zones.

24. The method of claim 23 wherein at least one of the liquid-retaining zones has a microvolume capacity of liquid retention.

25. The method of claim 23 wherein the zones comprise a coating or deposition of assay reagent.

26. The method of claim 25 wherein the assay reagent comprises nutrient medium.

27. The method of claim 25 wherein the assay reagent comprises at least one indicator substance.

28. The method of claim 27 wherein the indicator substance is a chromogenic indicator, a fluorescent indicator, a luminescent indicator or an electrochemical indicator.

29. The method of claim 23 wherein the zones are uniform size and each zone has a liquid retention capacity of about 0.01 to about 25 microliters.

30. The method of claim 29 wherein each zone has a liquid retention capacity of about 1 to about 2 microliters.

31. The method of claim 23 wherein the culture device comprises about 10 to about 10,000 liquid-retaining zones.

32. The method of claim 31 wherein the culture device comprises about 400 to about 600 liquid-retaining zones.

33. The method of claim 23 wherein the liquid-retaining zones comprise microvolume wells.

34. The method of claim 23 wherein the land area comprises a treated nanostructured film.

35. The method of claim 23 wherein the liquid-retaining zones comprise hydrophilic fiber material projecting from the hydrophobic material.

36. The method of claim 35 wherein at least one of the zones comprises a hydrophilic absorbent disc.

37. The method of claim 35 wherein at least one of the zones comprises protruding hydrophilic nonwoven fiber loop material.

38. The method of claim 23 wherein the culture device comprises a plurality of at least two sets of liquid-retaining zones, each set having zones of uniform size, the sets varying in liquid retention capacity.

39. A culture device for detection or enumeration of microorganisms, the device comprising an assay surface, the assay surface comprising liquid-retaining zones comprising a hydrophilic material and a land area comprising a hydrophobic material between the zones, at least one of the zones comprising an assay reagent.

40. The culture device of claim 39 wherein at least one of the liquid-retaining zones has a microvolume capacity of liquid retention.

41. The culture device of claim 39 wherein the device comprises about 10 to about 10,000 zones.

42. The culture device of claim 41 wherein the device comprises about 400 to about 600 zones.

43. The culture device of claim 39 wherein each zone has a liquid retention capacity of about 0.01 to about 25 microliters.

44. The culture device of claim 43 wherein each zone has a liquid retention capacity of about 1 to about 2 microliters.

45. The culture device of claim 39 wherein the assay reagent comprises a nutrient medium.

46. The culture device of claim 39 wherein the assay reagent comprises an indicator substance.

47. The culture device of claim 46 wherein the indicator substance is a chromogenic indicator, a fluorescent indicator, a luminescent indicator or an electrochemical indicator.

48. The culture device of claim 39 wherein the liquid-retaining zones comprise microvolume wells.

49. The culture device of claim 39 wherein the land area comprises a treated nanostructured film.

50. The culture device of claim 39 wherein the liquid-retaining zones comprise hydrophilic fiber material projecting from the hydrophobic material.

51. The culture device of claim 50 wherein at least one zone comprises a hydrophilic absorbent disc.

52. The culture device of claim 50 wherein at least one zone comprises protruding hydrophilic nonwoven fiber loop material.

53. The culture device of claim 39 wherein the culture device comprises a plurality of at least two sets of liquid-retaining zones, each set having zones of uniform size, the sets varying in liquid retention capacity.

54. A method for partitioning an aqueous liquid sample into discrete volumes to conduct a most probable number analysis, comprising:
 a) providing a device for culturing a microorganism, the device including an assay surface, the assay surface comprising liquid-retaining zones comprising a hydrophilic material and a land area comprising a hydrophobic material between the zones;
 b) contacting a liquid sample with the assay surface such that the liquid sample partitions into the liquid-retaining zones;
 c) incubating the device;
 d) detecting a signal that indicates microorganisms are growing in a zone; and
 e) conducting a most probable number analysis based on the number of zones wherein a signal is detected.

* * * * *